United States Patent
Colle et al.

(10) Patent No.: US 9,561,996 B2
(45) Date of Patent: Feb. 7, 2017

(54) KETO ACID ESTERS AS PVC PLASTICIZERS

(75) Inventors: Karla S. Colle, Magnolia, TX (US); Jorg F. Weber, Houston, TX (US); Allen D. Godwin, Seabrook, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 1255 days.

(21) Appl. No.: 13/378,959

(22) PCT Filed: Jun. 21, 2010

(86) PCT No.: PCT/US2010/039342
§ 371 (c)(1),
(2), (4) Date: Mar. 26, 2012

(87) PCT Pub. No.: WO2011/011137
PCT Pub. Date: Jan. 27, 2011

(65) Prior Publication Data
US 2012/0171397 A1    Jul. 5, 2012

Related U.S. Application Data

(60) Provisional application No. 61/227,116, filed on Jul. 21, 2009.

(51) Int. Cl.
| | |
|---|---|
| *C07C 45/68* | (2006.01) |
| *C07C 51/235* | (2006.01) |
| *C07C 67/03* | (2006.01) |
| *C07C 67/08* | (2006.01) |
| *C07C 67/313* | (2006.01) |
| *C07C 67/343* | (2006.01) |
| *C08K 5/10* | (2006.01) |
| *C08K 5/101* | (2006.01) |
| *C07C 45/72* | (2006.01) |
| *C07C 49/78* | (2006.01) |
| *C07C 49/86* | (2006.01) |
| *C07C 65/34* | (2006.01) |
| *C07C 69/76* | (2006.01) |
| *C07C 69/738* | (2006.01) |
| *C07C 69/82* | (2006.01) |
| *C08L 27/06* | (2006.01) |

(52) U.S. Cl.
CPC .............. *C07C 67/03* (2013.01); *C07C 45/68* (2013.01); *C07C 45/72* (2013.01); *C07C 49/78* (2013.01); *C07C 49/86* (2013.01); *C07C 51/235* (2013.01); *C07C 65/34* (2013.01); *C07C 67/08* (2013.01); *C07C 67/313* (2013.01); *C07C 67/343* (2013.01); *C07C 69/738* (2013.01); *C07C 69/76* (2013.01); *C07C 69/82* (2013.01); *C08K 5/10* (2013.01); *C08K 5/101* (2013.01); *C08L 27/06* (2013.01); *Y10T 428/139* (2015.01); *Y10T 428/1334* (2015.01); *Y10T 442/2369* (2015.04)

(58) Field of Classification Search
CPC ........ C07C 45/68; C07C 51/235; C07C 67/03; C07C 67/08; C07C 67/313; C07C 67/343; C07C 45/72; C07C 49/78; C07C 49/86; C07C 65/34; C07C 69/76; C07C 69/738; C07C 69/82; C08K 5/10; C08K 5/101; C08L 27/06; Y10T 428/139; Y10T 428/1334; Y10T 442/2369
USPC ...................................................... 524/287
See application file for complete search history.

(56) References Cited

U.S. PATENT DOCUMENTS

| | | | |
|---|---|---|---|
| 2,233,513 A | 3/1941 | Bruson | |
| 2,327,947 A | 8/1943 | Warmisham | |
| 2,566,205 A | 8/1951 | Hunn | |
| 5,068,393 A | 11/1991 | Maignan et al. | |
| 6,133,228 A * | 10/2000 | Pika ......................... | A61K 8/37 |
| | | | 512/21 |
| 6,740,254 B2 | 5/2004 | Zhou et al. | |
| 6,777,514 B2 | 8/2004 | Patil et al. | |
| 7,025,999 B2 | 4/2006 | Johnson et al. | |
| 2006/0247461 A1 | 11/2006 | Schlosberg et al. | |
| 2014/0100383 A1* | 4/2014 | Dakka ..................... | C07C 51/31 |
| | | | 560/51 |

FOREIGN PATENT DOCUMENTS

| | | |
|---|---|---|
| DE | 495 447 | 4/1930 |
| DE | 10 2005 062 029 | 6/2007 |
| EP | 1 505 054 | 2/2005 |
| WO | 99/32427 | 7/1999 |
| WO | 03/029339 | 4/2003 |
| WO | 2004/046078 | 6/2004 |
| WO | 2011/011137 | 1/2011 |

OTHER PUBLICATIONS

Arnoldi, A. et al., "*Synthesis and Structure-Activity Relationships of Sweet 2-Benzoylbenzoic Acid Derivatives*", J. Agric. and Food Chem., vol. 45(6), pp. 2047-2054 (1997).
Newman, M.S. et al., "*Studies on the Acid-Catalyzed Esterification of Substituted o-Benzoylbenzoic Acids in Methanol*", J. Org. Chem., vol. 30, pp. 1795-1800 (1965).
Small, P.A., "*Some Factors Affecting the Solubility of Polymers*", J. Appl. Chem., vol. 3, pp. 76-80 (1953).

(Continued)

*Primary Examiner* — Angela C Scott
(74) *Attorney, Agent, or Firm* — Darryl M. Tyus

(57) ABSTRACT

Resin plasticizers are produced by esterification of keto acids derived from acylation of aromatic compounds with cyclic anhydrides, and are particularly useful in making phthalate-free articles using PVC.

5 Claims, No Drawings

(56) References Cited

OTHER PUBLICATIONS

Godwin, "Plasticizers", Applied Polymer Science 21$^{st}$ Century, ed. Craver et al.,2000, pp. 157-175.
Hahn et al., "Ortho-Benzoyl-Benzoic Acids Containing Fluorine, Iodine and Sulfur", Journal of American Chemical Society, 1924, vol. 46, No. 7, pp. 1645-1653.
Jones et al., "2-Benzoylbenzoic Acid: A Photolabile Mask for Alcohols and Thiols", Journal of Organic Chemistry, 1996, vol. 61, No. 26, pp. 9455-9461.
Kiryanov et al., "Synthesis and Mesomorphic Properties of 1,1-Difluoroalkyl-Substituted Biphenylthienyl and Terphenyl Liquid Crystals. A Comparative Study of Mesomorphic Behavior Relative to Alkyl, Alkoxy and Alkanoyl Analogs", Journal of Materials Chemistry, 2001, vol. 11, No. 12, pp. 3068-3077.
Rubidge et al., "Friedel and Crafts' Reaction—The Preparation of Orthobenzoyl-Benzoic Acid and Benzophenone", Journal of the American Chemical Society, 1914, vol. 36, No. 4, pp. 732-737.
Sonpatki et al., "Troublesome Alkoxythiophenes. A Highly Efficient Synthesis via Cylization of Gamma-Keto Esters", Journal of Organic Chemistry, 2001, vol. 66, No. 22, pp. 7283-7286.
Zymalkowski et al., "Die Reduktion Von Beta-Benzoyl-Propionsaeuren Aus Der Reihe Des Resorcins", Archiv Der Pharmazie Und Berichte Der Deutschen Pharmazeutischen Gesellschaft, 1966, vol. 299, No. 6, pp. 545-559.

\* cited by examiner

KETO ACID ESTERS AS PVC PLASTICIZERS

CROSS-REFERENCE TO RELATED APPLICATIONS

This application is a 371 National Stage Application of International Application No. PCT/US2010/039342, filed Jun. 21, 2010, which claims the benefit of Ser. No. 61/227,116, filed Jun. 21, 2009, the disclosure of which is incorporated herein by reference in its entirety.

FIELD OF THE INVENTION

The invention relates to keto acid esters based on branched alkyl groups, useful as plasticizers and viscosity depressants for a wide range of resins, particularly PVC resin.

BACKGROUND OF THE INVENTION

Plasticizers are incorporated into a resin (usually a plastic or elastomer) to increase the flexibility, workability, or distensibility of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, poly (vinylidene chloride), nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Plasticizers can be characterized on the basis of their chemical structure. The most important chemical class of plasticizers is phthalic acid esters, which accounted for about 85% worldwide of PVC plasticizer usage in 2002. However, in the recent past there as been an effort to decrease the use of phthalate esters as plasticizers in PVC, particularly in end uses where the product contacts food, such as bottle cap liners and sealants, medical and food films, or for medical examination gloves, blood bags, and IV delivery systems, flexible tubing, or for toys, and the like. For these and most other uses of plasticized polymer systems, however, a successful, general purpose substitute for phthalate esters has heretofore not materialized on a commercial scale.

One such suggested substitute for phthalates are esters based on cyclohexanoic acid. In the late 1990's and early 2000's, various compositions based on cyclohexanoate, cyciohexanedioates, and cyclohexanepolyoate esters were said to be useful for a range of goods from semi-rigid to highly flexible materials. See, for instance, WO 99/32427, WO 2004/046078, WO 2003/029339, WO 2004/046078, U.S. Application No. 2006-0247461, and U.S. Pat. No. 7,297,738.

Other suggested substitutes include esters based on benzoic acid (see, for instance, U.S. Pat. No. 6,740,254, and also co-pending, commonly-assigned, U.S. Provisional Application 61/040,480, polyketones, such as described in U.S. Pat. No. 6,777,514; and also co-pending, commonly-assigned, U.S. Provisional application Ser. No. 12/058,397, and triglycerides, such as described in co-pending, commonly assigned, U.S. Provisional Application 61/040,490. Epoxidized soybean oil (ESO), which has much longer alkyl groups (C16 to C18) has been tried as a plasticizer, but is generally used as a PVC stabilizer in low concentrations. At higher concentrations, ESO exudaton can occur.

Typically, the best that has been achieved with substitution of the phthalate ester with an alternative material is a flexible PVC article having either reduced performance or poorer processability. Thus, heretofore efforts to make phthalate-free plasticizer systems for PVC have not proven to be entirely satisfactory, and this is still an area of intense research.

U.S. Pat. No. 2,233,513 teaches aroylbenzoic acid esters with nitrocellulose and acetylcellulose. Nitrocellulose and acetylcellulose are resins used in centuries-old technology and find only limited use today. These materials are very brittle without plasticizer. The most common plasticizer for these resins was camphor. In part because of the odor imparted to the final product caused by the use of camphor, there were constant efforts to find alternative plasticizers. In general for every polymer, you need to have a plasticizer with the correct balance of solvating properties, volatility, and so forth. In the case of nitrocellulose, most of these efforts to find replacement plasticizers were in the area of improving the processability, stability, and decrease the brittleness of rigid or semi-rigid nitrocellulose products. The first applications of nitrocellulose were for ivory substitutes in billiard balls, false teeth, and piano keys. Here the plasticizers help greatly in processing and to reduce the brittleness of these rigid products. Later applications of nitrocellulose were in the area of stiff brush or combs, which had, before the use of nitrocellulose, been made from natural products. Eventually nitrocellulose found use in motion picture film. However, while "plasticizing" such resins made them more impact resistant and durable, this technology was rapidly replaced, over the span of barely a decade, with the introduction of PVC-based resins. In contrast to the cellulosic resins, PVC may be made truly flexible by plasticizing with the appropriate materials. Accordingly, there is no reason to assume that a plasticizer used with cellulosic material can be used successfully with PVC. Camphor, for instance, is not a good plasticizer of PVC. The same is seen with plasticizers used in polyvinyl butryal (PVB)—generally successful plasticisers of PVB resin are not useful in PVC. Plasticizers used in these polymers are not necessarily good plasticizers.

Accordingly, the industry still seeks a general purpose non-phthalate plasticizer, particularly a plasticizer that has a suitable melting or pour point, increased compatibility with the resin, and providing a PVC composition having good performance and low temperature properties, wherein the plasticizer can be made by a process having a high throughput and using readily available raw materials.

In U.S. Pat. No. 2,372,947, alkyl esters of ortho-henzoyl benzoic acid are described as being useful in polyvinyl halide resins.

The present inventors have surprisingly discovered that keto acid esters have advantageous properties when used in PVC and furthermore can readily made by esterifying alcohols with keto acids, the keto acids preferably being derived by acylating an aromatic molecule with a cyclic anhydride.

SUMMARY OF THE INVENTION

The invention is directed to keto acid esters and their use as plasticizers with resins selected from PVC, PVC copolymers, acrylic polymers and copolymers, and polyurethanes.

In embodiments, the keto acid esters are derived by acylating an aromatic molecule, such as benzene, toluene, one or more xylenes, anisole and other aromatic ethers, or mixtures of aromatic molecules, in a Friedel-Crafts type reaction, with a cyclic anhydride, such as succinic anhydride, phthalic anhydride, and the like. The resulting keto acid is esterified using an alcohol.

In embodiments the alcohol are derived from C6 to C13 aldehydes obtained from a hydroformylation process.

In preferred embodiments, the process further comprises providing a feed for the hydroformylation process from dimerization of diverse feedstock, preferably dimerization of a C3 or C4 feedstock, or a mixture thereof.

The invention is also directed to keto acid esters, particularly keto acid esters derived from branched C7 to C13 alcohols, and also to compositions including a resin, such as PVC, and a keto acid ester according to the invention.

In embodiments, the alcohols esterified with the keto acids have an average branching of from about 0.8 to about 3.0 branches per molecule. In an embodiment, the average branching may range from about 1.0 to about 2.4. In another embodiment, the average branching of the C5 to C8 alkyl groups ranges from about 1.2 to about 2.2, preferably around about 1.2 to about 2.0, more preferably about 1.2 to about 1.8 branches per molecule. In embodiments the average branching will be from about 1.2 to about 1.6.

The invention is still further directed to an article comprising the composition according to the invention.

It is an object of the invention to provide a plasticizer suitable for diverse resins such as poly (vinyl chloride), acrylic polymers, and polyurethanes.

It is another object of the invention to provide a high throughput process for producing keto acid esters suitable for plasticizing resin, especially PVC.

It is yet another object of the invention to provide phthalate-free compositions and articles.

These and other objects, features, and advantages will become apparent as reference is made to the following detailed description, preferred embodiments, examples, and appended claims.

DETAILED DESCRIPTION OF THE INVENTION

The invention is directed to keto acid esters and their use as plasticizers, particularly with PVC resins.

In embodiments, the keto acid esters are derived by acylating an aromatic molecule, such as benzene, toluene, one or more xylenes, anisole or other aromatic ethers, or mixtures of aromatic molecules, in a Friedel-Crafts type or condensation reaction, with a cyclic anhydride, such as succinic anhydride, phthalic anhydride, and the like. The resulting keto acid is esterified using an alcohol.

In embodiments the alcohol are derived from C6 to C13 aldehydes obtained from a hydroformylation process.

In preferred embodiments, the process further comprises providing a feed for the hydroformylation process from dimerization of diverse feedstock, preferably dimerization of a C3 or C4 feedstock, or a mixture thereof.

The invention is also directed to keto acid esters, particularly keto acid esters wherein the alcohol moiety is derived from branched C6 to C13 alcohols, and also to compositions including a resin, such as PVC, and a keto acid ester according to the invention.

The keto acid esters of the invention are derived by acylating an aromatic molecule such as benzene, toluene, anisole or other aromatic ethers, one or more xylenes, or mixtures of aromatic molecules. Typical aromatic molecules useful in this reaction include benzene, toluene, xylenes, propylbenzene, cumene, tort-butylbenzene, sec-butylbenzene, isobutylbenzene, isopentylbenzene, (1,2-dimethylpropyl)-benzene, pentylbenzene, 1-phenylhexane, heptylbenzene, 1-phenyloctane, 1-phenylnonane, undecylbenzene, 1-phenylundecane, 1-phenyldodecane, 1-phenyltridecane, tetradecylbenzene, 1-phenyltetradecane, 1-phenylpentadecane, hexadecylbenzene, anisole, veratrole, naphthalene and substituted naphthalenes.

The cyclic anhydride may be selected from at least one of phthalic anhydride, succinic anhydride, maleic anhydride, cyclohexanedicarboxylic anhydride, methylsuccinic anhydride, 2,2-dimethylsuccinic anhydride, hexabydro-4-methylphthalic anhydride, itaconic anhydride, norbornene-dicarboxylic anhydride, glutaric anhydride, dimethylglutaric anhydride, epoxy-tetrahydrophthalic anhydride, tetrahydrophthalic anhydride, diglycolic anhydride, 2-phenylglutaric anhydride, homophthalic anhydride, and methylphthalic anhydride.

Acylation reactions with cyclic anhydrides are well-known per se (see Friedel-Crafts and Related Reaction, George Olah, Ed., Vol. 3 Part 1, Chapter XXXIV "Acylation with Di- and Polycarboxylic Acid Derivatives" by Andrew G. Peto, interscience, 1964, for example). An aromatic keto acid is produced when an aromatic compound is reaction with a cyclic anhydride in the presence of an acidic catalyst. The catalyst may be a Lewis acid catalyst, such as $AlCl_3$, a protonic acid or solid acid catalysts, such as zeolites or sulfated zirconia, among others.

In embodiments the alcohol are derived from C6 to C13 aldehydes obtained from a hydroformylation process, and in preferred embodiments, the process further comprises providing a feed for the hydroformylation process from dimerization of diverse feedstock, preferably oligomerization, such as dimerization or trimerization, of a feedstock selected from C3 to C6 olefins.

In embodiments, the alcohol with which the keto acid is esterified will have an average branching of from about 0.8 to about 3.0. In an embodiment, the average branching may range from about 1.0 to about 2.4. In another embodiment, the average branching will range from about 1.2 to about 2.2, preferably around about 1.2 to about 2.0, more preferably about 1.2 to about 1.8 branches per molecule.

Branching may be determined by known NMR methods, such as employed in U.S. Pat. No. 6,437,170. Branching may also be attenuated by one of ordinary skill in the art by appropriate process conditions and reagents. In embodiments the branching in these alcohols may be almost exclusively methyl branches but some ethyl branches may also be present in small amounts.

In an embodiment, the process of the invention further comprises the production of branched aldehydes by hydroformylation of C5 to C13 olefins that in turn have been produced by oligomerization of propylene and/or butene over solid phosphoric acid or zeolite catalysts or nickel based dimerzation technologies or through the Dimersol process. These oligomerization processes are per se well-known. See, for instance, U.S. Pat. No. 7,253,330, and U.S. Pat. No. 7,145,049.

The resulting C6 to C13 aldehydes are then hydrogenated to yield the corresponding primary alcohols.

The plasticizers of this invention can then be prepared through the esterification of the keto acids with these C6 to C13 alcohols.

The production of the keto acids and then corresponding esters, according to the invention may be conveniently exemplified by the following reactions, shown schematically. These reaction schemes are depicted with mono-substituted aromatics but a wide range of aromatics may be used. For example, benzene (R=H), toluene (R=CH3, xylenes (disubstituted with two R—CH3 groups). Similarly, R'OH may cover a range of alcohols, such as described previously.

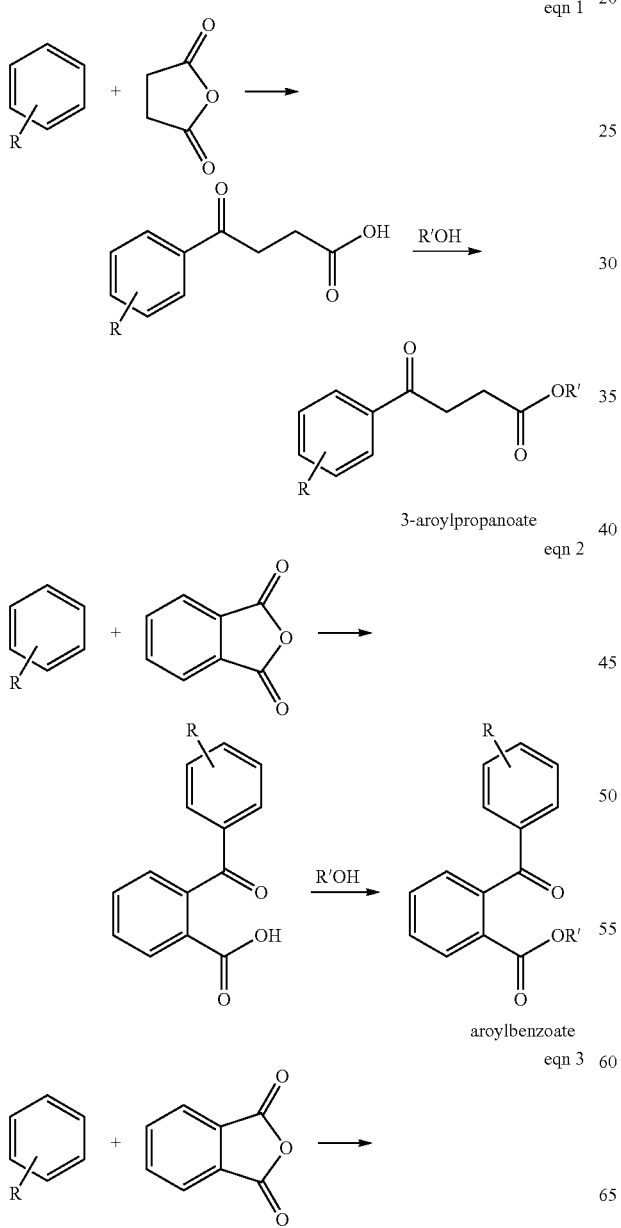

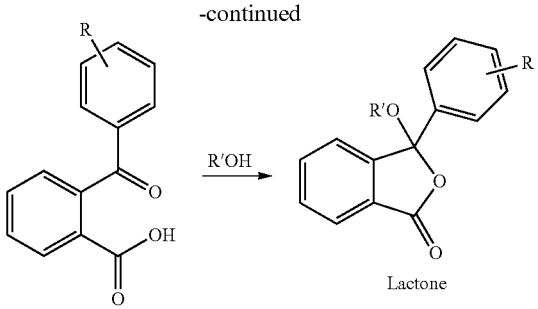

In the case of the aroyl benzoic acid molecule derived from phthalic anhydride, shown in equation 2, the esterification can also yield another isomeric structure via rearrangement, as shown in equation 3. The final esterification product can be a mixture of the ester shown in equation 2 and the lactone shown in equation 3.

Another synthetic route to the keto acids of the invention is by the method illustrated below, wherein the alkyl groups on R1 may be selected from linear or branched alkyls, preferably having from 1 to 6 carbon atoms.

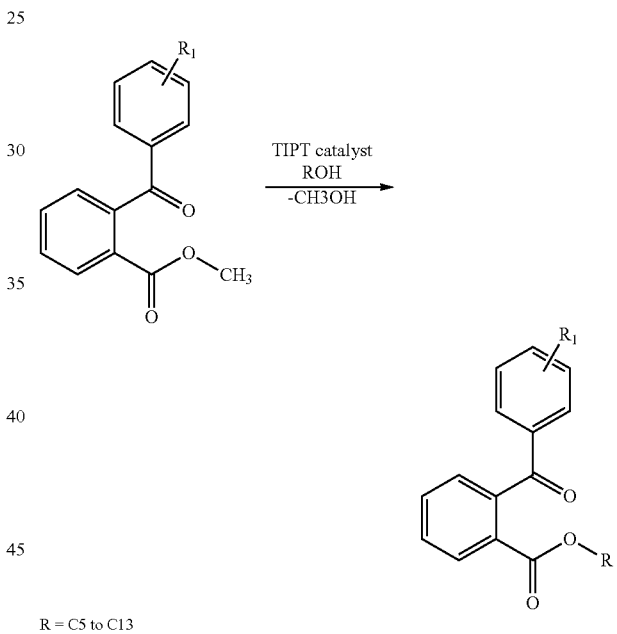

R = C5 to C13
R1 = Alkyl

Example 1

General procedure for synthesis of the plasticizer by esterification. Into a four necked 1000 ml round bottom flask equipped with an air stirrer, nitrogen inductor, thermometer, Dean-Stark trap and chilled water cooled condenser were added keto acid and Oxo alcohol in a mole ratio of 1:2. The reaction mixture was heated to 220° C. with air stirring under a nitrogen sweep. The water evolved during the esterification reaction was collected in the Dean-Stark trap and was drained frequently and monitored until approximately theoretical weight was collected, indicating near complete reaction. The excess alcohol were removed by distillation or steam stripping. In some instances, titanium isopropoxide was used as a catalyst for the esterification reaction.

Table 1 summarizes the aroyl benzoates prepared from the reaction of an aromatic with phthalic anhydride. A general structure for the aroyl benzoates is shown below:

TABLE 1

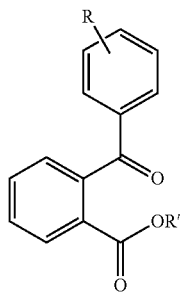

| R | R' |
|---|---|
| H | $C_6H_{13}$ |
| H | $C_9H_{19}$ |
| H | $C_{10}H_{21}$ |
| H | $C_{12}H_{25}$ |
| H | $C_{13}H_{27}$ |
| $CH_3$ | $C_5H_{11}$ |
| $CH_3$ | $C_6H_{13}$ |
| $CH_3$ | $C_9H_{19}$ |

Table 2 summarizes the aroyl propionates prepared from the reaction of an aromatic with succinic anhydride. A general structure for the aroyl propionates is shown below:

TABLE 2

| R | R' |
|---|---|
| H | $C_9H_{19}$ |
| H | $C_{13}H_{27}$ |
| $CH_3$ | $C_9H_{19}$ |
| $CH_3$ | $C_{13}H_{27}$ |
| 2 $CH_3$ * | $C_9H_{19}$ |
| 2 $CH_3$ * | $C_{10}H_{21}$ |
| $t$-$C_4H_9$ | $C_9H_{19}$ |

* 1,3-dimethylbenzene

Example 1

Plasticization

Formulations corresponding to Table 3, were mixed at room temperature with moderate stirring, then placed on a roll mill at 340° F. and milled for 6 minutes. The flexible vinyl sheet was removed and compression molded at 350° F.

Sample A DINP=di-isononylphthalate
Sample B TBA-9=iso-nonyl toluoyl benzoate
Sample C TPA-9=iso-nonyl toluoyl propionate

TABLE 3

| Formulation | -A | -B | -C |
|---|---|---|---|
| PVC | 100 | 100 | 100 |
| Plasticizer | DINP | TBA-9 | TPA-9 |
| Phr | 50 | 50 | 50 |
| ESO | 3 | 3 | 3 |
| CuZn Stabilizer | 3 | 3 | 3 |
| stearic acid | 0.25 | 0.25 | 0.25 |

Comparison of the data for the formulations follows:

TABLE 4

Mechanical Properties Comparison

| Sample ID | A | B | C |
|---|---|---|---|
| Original Mechanical Properties | | | |
| Shore A Hardness (15 sec.) | 78.0 | 79.2 | 71.6 |
| 95% Confidence Interval | 0.5 | 0.6 | 2.3 |
| Shore D Hardness (15 sec.) | 26.1 | 28.5 | 21.0 |
| 95% Confidence Interval | 0.3 | 0.5 | 0.3 |
| 100% Modulus Strength, psi | 1668 | 2123 | 1233 |
| 95% Confidence Interval | 26 | 30 | 33 |
| Ultimate TensileStrength, psi | 2987 | 3351 | 3116 |
| 95% Confidence Interval | 174 | 35 | 56 |
| Ultimate Elongation, % | 322 | 309 | 364 |
| 95% Confidence Interval | 31 | 13 | 13 |
| Aged Mechanical Properties: 7 Days at 100° C. (AC/hour) | | | |
| Aged 100% Modulus Strength, psi | 2114 | 2611 | — |
| 95% Confidence Interval | 13 | 24 | — |
| Ultimate TensileStrength, psi | 2822 | 2997 | 5869 |
| 95% Confidence Interval | 86 | 88 | 336 |
| Ultimate Elongation, % | 265 | 214 | 28 |
| 95% Confidence Interval | 20 | 17 | 11 |
| Weight Loss, Wt % | 5.9 | 6.2 | 20.7 |
| 95% Confidence Interval | 0.28 | 0.12 | 0.28 |
| Retained Properties: 7 Days at 100° C. (AC/hour) | | | |
| Retained 100% Modulus Strength, % | 127 | 123 | — |
| 95% Confidence Interval | 0.4 | 0.3 | — |
| Retained Tensile Strength, % | 94 | 89 | 188 |
| 95% Confidence Interval | 0.4 | 0.3 | 0.7 |
| Retained Elongation, % | 82 | 69 | 8 |
| 95% Confidence Interval | 1.7 | 1.4 | 0.9 |
| Low Temperature | | | |
| Clash Berg (Tf), C. | −21.9 | 3.8 | −18.9 |
| 95% Confidence Interval | 0.8 | 1.2 | 1.2 |

Samples were milled at 340° F. and molded at 350° F. to thickness. Conditioning was 7 days prior to testing

TABLE 4a

Mechanical Properties Comparsion
TSR # 09-020 "Wet Blends"

| Sample ID: | D | E |
|---|---|---|
| Formulations: | | |
| PVC (Oxy 240) | 100 | 100 |
| isodecylbenzoylbenzoate (BBA-10) | 50 | |
| Jayflex DINP | | 50 |
| ESO (Drapex 6.8) | 3 | 3 |
| CaZn stabilizer (Mark 1221) | 2.5 | 2.5 |
| Stearic Acid | 0.25 | 0.25 |
| Sample Prep & Observations: | | |
| Samples were milled at 330° F. and molded at 340° F. | Low-moderate smoking; low odor | Low-moderate smoking; low odor |

TABLE 4a-continued

Mechanical Properties Comparsion
TSR # 09-020 "Wet Blends"

| Sample ID: | D | E |
|---|---|---|
| Original Mechanical Properties | | |
| Shore A Hardness (15 sec.) | 76.8 | 78.5 |
| 95% Confidence Interval | 1.2 | 1.1 |
| 100% Modulus Strength, psi | 2013 | 1674 |
| 95% Confidence Interval | 67 | 22 |
| Ultimate TensileStrength, psi | 3319 | 3221 |
| 95% Confidence Interval | 99 | 50 |
| Ultimate Elongation, % | 301 | 375 |
| 95% Confidence Interval | 15 | 7 |
| Aged Mechanical Properties: | | |
| Aged 100% Modulus Strength, psi | 2719 | 2249 |
| Aged Ultimate TensileStrength, psi | 162 | 85 |
| Ultimate TensileStrength, psi | 3082 | 3094 |
| 95% Confidence Interval | 105 | 101 |
| Ultimate Elongation, % | 206 | 299 |
| 95% Confidence Interval | 32 | 12 |
| Weight Loss, Wt % | 10 | 6.9 |
| 95% Confidence Interval | 1.03 | 0.61 |
| Retained Properties: | | |
| Retained 100% Modulus Strength, % | 135 | 134 |
| 95% Confidence Interval | 0.7 | 0.6 |
| Retained Tensile Strength, % | 93 | 96 |
| 95% Confidence Interval | 0.3 | 0.3 |
| Retained Elongation, % | 68 | 80 |
| 95% Confidence Interval | 1.7 | 0.8 |
| Other: | | |
| Carbon Volatility (24 hours at 70 C.) | | |
| Mean (3 specimens) | 0.5 | 0.5 |
| 95% Confidence Interval | 0 | 0.1 |
| Low Temperature | | |
| Bell Brittleness (Tb), C. | −1.8 | −30.2 |
| 95% Confidence Interval | 2 | 2 |

TABLE 5

Mechanical Properties Comparison
TSR # 09-021
"Plastisols"

| Sample ID: | F | G |
|---|---|---|
| Formulations: | | |
| PVC Plastisol (GEON 124A) | 100 | 100 |
| iso-decyl benzoylbenzoate | 70 | |
| Jayflex DINP | | 70 |
| (ESO) Drapex 6.8 | 2 | 2 |
| (Ca/Zn Stabilizer) Mark 1221 | 2.5 | 2.5 |
| Sample Prep & Observations: | | |
| Samples were fused on WM Oven at 190° C. and molded at 340° F. to thickness. | | |
| Original Mechanical Properties | | |
| Shore A Hardness (15 sec.) | 61 | 63 |
| 95% Confidence Interval | 0.4 | 0.8 |
| 100% Modulus Strength, psi | 980 | 975 |
| 95% Confidence Interval | 24 | 14 |
| Ultimate TensileStrength, psi | 2389 | 2318 |
| 95% Confidence Interval | 74 | 90 |
| Ultimate Elongation, % | 334 | 384 |
| 95% Confidence Interval | 67 | 12 |
| Aged Mechanical Properties: | | |
| Aged 100% Modulus Strength, psi | 1794 | 1379 |
| Aged Ultimate TensileStrength, psi | 173 | 29 |
| Ultimate TensileStrength, psi | 2460 | 2114 |

TABLE 5-continued

Mechanical Properties Comparison
TSR # 09-021
"Plastisols"

| Sample ID: | F | G |
|---|---|---|
| 95% Confidence Interval | 209 | 40 |
| Ultimate Elongation, % | 232 | 253 |
| 95% Confidence Interval | 27 | 9 |
| Weight Loss, Wt % | 14 | 11 |
| 95% Confidence Interval | 0.43 | 0.28 |
| Retained Properties: | | |
| Retained 100% Modulus Strength, % | 183 | 141 |
| 95% Confidence Interval | 1.4 | 0.7 |
| Retained Tensile Strength, % | 103 | 91 |
| 95% Confidence Interval | 0.5 | 0.3 |
| Retained Elongation, % | 70 | 66 |
| 95% Confidence Interval | 1.6 | 0.7 |

TABLE 6

Mechanical Properties Comparison
TSR # 09-027
"Wet-Blends"

| Sample ID | H | I |
|---|---|---|
| Formulations: | | |
| Oxy 240 | 100 | 100 |
| iso-nonyl benzoylpropionate | 50 | |
| iso-nonyl benzoylbenzoate | | 50 |
| Drapex 6.8 (ESO) | 2.5 | 2.5 |
| Mark 1221 (CaZn Stabilizer) | 2.5 | 2.5 |
| Stearic Acid (External Lubricant) | 0.3 | 0.3 |
| Sample Prep & Observations | | |
| Samples were milled at 330° F. and molded at 340° F. | Moderate smoking; High odor | Low smoking; low odor |
| Original Mechanical Properties | | |
| Shore A Hardness (15 sec.) | 73 | 79 |
| 95% Confidence Interval | 0.64 | 0.80 |
| Shore D Hardness (15 sec.) | 21 | 27 |
| 95% Confidence Interval | 0.14 | 0.14 |
| 100% Modulus Strength, psi | 1276 | 2011 |
| 95% Confidence Interval | 35 | 32 |
| Ultimate TensileStrength, psi | 3148 | 3403 |
| 95% Confidence Interval | 122 | 129 |
| Ultimate Elongation, % | 357 | 296 |
| 95% Confidence Interval | 13 | 20 |
| Aged Mechanical Properties: | | |
| Aged 100% Modulus Strength, psi | 1640 | 2146 |
| 95% Confidence Interval | 109 | 30 |
| Ultimate TensileStrength, psi | 3131 | 3211 |
| 95% Confidence Interval | 99 | 123 |
| Ultimate Elongation, % | 309 | 279 |
| 95% Confidence Interval | 23 | 16 |
| Weight Loss, Wt % | 5 | 1 |
| 95% Confidence Interval | 1.4 | 0.4 |
| Retained Properties: | | |
| Retained 100% Modulus Strength, % | 129 | 107 |
| 95% Confidence Interval | 0.86 | 0.33 |
| Retained Tensile Strength, % | 99 | 94 |
| 95% Confidence Interval | 0.40 | 0.38 |
| Retained Elongation, % | 87 | 94 |
| 95% Confidence Interval | 1.4 | 1.7 |
| Low Temperature | | |
| Clash Berg (Tf), C. | −20 | −0.2 |
| 95% Confidence Interval | 2.4 | 1.6 |

The plasticizers according to the invention may also be used with vinyl chloride-type resins, polyesters, polyurethanes, ethylene-vinyl acetate copolymer, rubbers, acrylics, polymer blends such as of polyvinyl chloride with an ethylene-vinyl acetate copolymer or polyvinyl chloride with a polyurethane or ethylene-type polymer.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The invention has been described above with reference to numerous embodiments and specific examples. Many variations will suggest themselves to those skilled in this art in light of the above detailed description. All such obvious variations are within the full intended scope of the appended claims.

What is claimed is:

1. A process for producing keto acid esters, the process comprising:
    (a) a first step of Friedel crafts reaction of benzoyl chloride with benzene in the presence of an acidic catalyst comprising AlCl$_3$ to form benzophenone, a second step reaction of benzophenone with CO/HCl in a Gattermann-Koch reaction to form benzophenone aldehyde, a third step of the oxidation of the aldehyde to the acid, a fourth step of the esterification with an ROH alcohol, as illustrated in the following scheme:

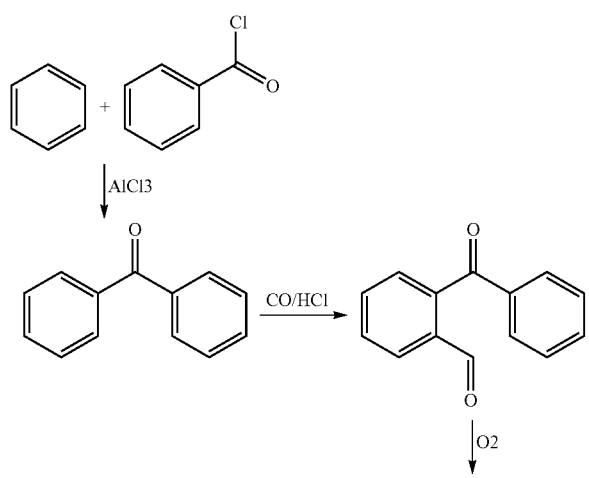

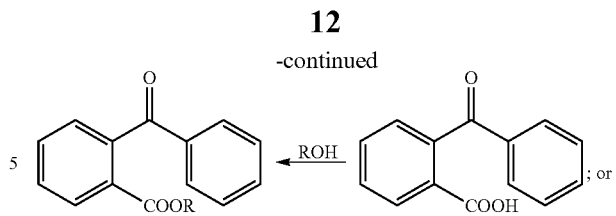

(b) a first step reaction of benzoate ester with CO/HCl in a Gatterman-Koch reaction, a second step formation of acid chloride in the presence of SOCl$_2$, a third reaction Friedel Crafts acylation in the presence of benzene and AlCl$_3$, as illustrated in the following schematic:

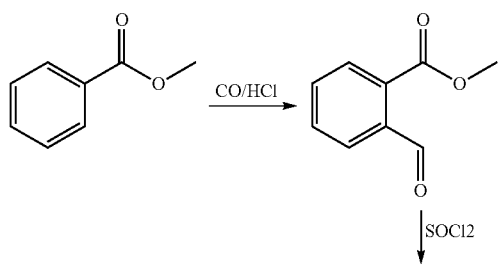

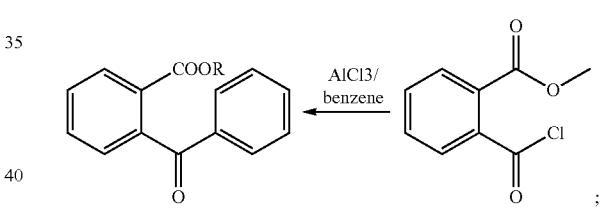

wherein said ROH alcohol comprises a C6 to C13 alcohol derived from the oligomerization of at least one C3-C6 olefin to form an oligomer, followed by hydroformylation and hydrogenation reactions of said oligomer to form said C6 to C13 alcohol.

2. The process of claim 1, wherein said hydroformylation reaction is catalyzed by a metal selected from Rh, Co, and mixtures thereof.

3. The process of claim 1, wherein said hydroformylation reaction is catalyzed by Co.

4. The process of claim 1, wherein said hydroformylation reaction is catalyzed by Rh.

5. The process of claim 1, wherein said oligomerization is catalyzed by solid phosphoric acid, a zeolite, or a combination thereof.

* * * * *